United States Patent [19]

Gaulton et al.

[11] Patent Number: 5,736,360
[45] Date of Patent: Apr. 7, 1998

[54] ENDOTHELIAL CELL TROPIC COMPOSITIONS AND METHODS OF MAKING AND USING THE SAME

[75] Inventors: Glen Gaulton, Havertown; Ben Ho Park, Philadelphia, both of Pa.

[73] Assignee: The Trustees of the University of Pennsylvania, Philadelphia, Pa.

[21] Appl. No.: 612,890

[22] PCT Filed: Sep. 9, 1994

[86] PCT No.: PCT/US94/10088

§ 371 Date: Jun. 30, 1996

§ 102(e) Date: Jun. 30, 1996

[87] PCT Pub. No.: WO95/07360

PCT Pub. Date: Mar. 16, 1995

Related U.S. Application Data

[63] Continuation-in-part of Ser. No. 121,051, Sep. 10, 1993, abandoned.

[51] Int. Cl.⁶ .......................... C12P 21/02; C12P 15/63; C12P 15/85
[52] U.S. Cl. .................. 435/69.1; 435/172.3; 435/320.1
[58] Field of Search .................. 536/23.1; 435/172.3, 435/69.1, 320.1

[56] References Cited

PUBLICATIONS

Engelhardt, J. et al., "Retrovirus Vector–Targeted Inducible Expression of Human β–Interferon Gene to B–Cells", *Virology* 1990, 178, 419–428.

Portis, J. et al., "the R–U5–5' Leader Sequence of Neurovirulent Wild Mouse Retrovirus Contains an Element Controlling the Incubation Period of Neurodegenerative Disease", *J. of Virology* 1991, 65 (4), 1877–1883.

Sambrook, J. et al., "Molecular Cloning A Laboratory Manual", Second Edition, Cold Spring Harbor Press, 1989, p. 16.4.

Yao, S.-N. et al., "Expression of Human Factor IX in Rat Capillary Endothelial Cells: Toward Somatic Gene Therapy for Hemophilia B", *PNAS USA* 1991, 88, 8101–8105.

Zwiebel, J. et al., "High–level Recombinant Gene Expression in Rabbit Endothelial Cells Transduced by Retroviral Vectors", *Science* Jan. 13, 1989, 243, 220–222.

Benditt et al., "Viruses in the Etiology of Atherosclerosis", *PNAS USA* 1983, 80, 6386–6389.

Debs et al., "Regulation of Gene Expression in Vivo by Liposome–Mediated Delivery of a Purified Transcription Factor", *J. Biol. Chem.* 1990, 265 (18), 10189–10192.

DesGroseillers et al., "Retrovirus–Induced Spongiform Encephlopathy: The 3'–End Long Terminal Repeat–Containing Viral Sequences Influence the Incidence of the Disease and the Specificity of the Neurological Syndrome", *PNAS USA* 1985, 82, 8818–8822.

ElDadah et al., "Viral Hemorrhagic Encephalopathy of Rats", *Science* 1967, 156, 392–394.

Landau et al., "Packaging System for Rapid Production of Murine Leukemia Virus Vectors with Variable Tropism", *J. Virol.* 1992, 66 (8), 5110–5114.

O'Hara et al., "Nucleotide Sequence of the Gene Coding for Human Factor VII, a Vitamin K–Dependent Protein Participating in Blood Coagulation", *PNAS USA* 1987, 84, 5158–5162.

Zhu et al., "Systemic Gene Expression After Intravenous DNA Delivery into Adult Mice", *Science* 1989, 261, 209–211.

*Primary Examiner*—Stephanie W. Zitomer
*Attorney, Agent, or Firm*—Woodcock Washburn Kurtz Mackiewicz & Norris LLP

[57] ABSTRACT

An isolated nucleic acid molecule comprising a modified Murine Leukemia Virus Long Terminal Repeat sequence that is capable of tropically regulating expression of operably linked coding sequences in a vessel endothelial cell is disclosed. A method of producing a non-Murine Leukemia Virus protein in a vessel endothelial cell is disclosed. The method comprises the step of introducing into the cell a nucleic acid molecule that comprises a modified Murine Leukemia Virus Long Terminal Repeat sequences operably linked to a nucleotide sequence which encodes a non-Murine Leukemia Virus protein, the modified Murine Leukemia Virus Long Terminal Repeat sequences being capable of tropically regulating expression in vessel endothelial cells.

26 Claims, No Drawings

ENDOTHELIAL CELL TROPIC COMPOSITIONS AND METHODS OF MAKING AND USING THE SAME

CROSS REFERENCE TO RELATED APPLICATIONS

This application is a 371 filing of PCT/US94/1088 filed Sep. 9, 1994 which is a continuation-in-part of U.S. application Ser. No. 08/121,051 filed Sep. 10, 1993, now abandoned, the disclosure of which is hereby incorporated by reference.

FIELD OF THE INVENTION

The present invention relates to genetic regulatory sequences that direct vessel endothelial cell specific expression of genes, chimeric genes comprising the regulatory sequence linked to coding sequences and to methods of producing proteins in endothelial cells using the chimeric genes.

BACKGROUND OF THE INVENTION

Advances in molecular biology over the past few decades have created new technologies for combating human disease. In particular, the transduction of foreign genes into somatic cells, or gene therapy, has shown great promise as a powerful clinical tool. Gene therapy has been used experimentally to correct disorders such as ADA deficiency and new trials are underway for treating other genetic diseases such as cystic fibrosis and muscular dystrophy. Most gene therapy studies to date have focused on correcting single gene defects by introducing the wild type gene into somatic cells. The product of the newly transduced gene then restores the normal phenotype. Other recent application include targeting tumor cells with neo-antigens for enhanced recognition by the immune system. Additionally, biologically active proteins may be delivered to an individual by the introduction and expression of foreign genes encoding such proteins.

Many studies have used bone marrow or bone marrow derived cells as targets for gene therapy. However, there has been a recent surge of interest in using other cell types, particularly endothelial cells. Endothelial cells represent an ideal target for gene therapy in many diseases. Endothelial cells are particularly useful in the treatment of hematological and vascular disorders as well as any disease that requires the systemic deliver of therapeutic factors.

Broader applicability of gene therapy has been hindered due to technical limitations. Most studies thus performed have been so using infected tissue ex vivo and then reconstituting the host with the genetically altered cells. While this practice is acceptable for tissues that can be harvested and re-implanted with relative ease, many desired target cells do not fall into this category. For this reason, the search for and/or creation of vectors that are expressed by specific tissues is an area of intense research interest. There is a need for regulatory elements which can be used to direct expression of foreign genes and endothelial cells. There is a need to create tissue specific vectors for in vivo gene therapy. There is a need to provide gene therapy constructs with regulatory elements that will direct tissue specific expression of the foreign genes.

SUMMARY OF THE INVENTION

The present invention relates to isolated nucleic acid molecules that comprise a modified Murine Leukemia Virus Long Terminal Repeat which comprises SEQ ID NO:4. In some embodiments, such nucleic acid molecules may comprise SEQ ID NO:3, SEQ ID NO:2 or SEQ ID NO:1.

The present invention relates to isolated nucleic acid molecules that comprise a modified Murine Leukemia Virus Long Terminal Repeat which comprises SEQ ID NO:4 and is operably linked to a nucleotide sequence that encodes a non-Murine Leukemia Virus. In some embodiments, such nucleic acid molecules may comprise SEQ ID NO:3, SEQ ID NO:2 or SEQ ID NO:1. In some embodiments, the non-Murine Leukemia Virus protein is a human protein, such as for example Factor VII protein, Factor IX protein, von Willdebrand factor, complement proteins, insulin, cytokines, tissue plasminogen activator, alpha-L-iduronidase, iduronate sulfatase, heparin, N-sulfatase and alpha 1 antitrypsin.

The present invention relates to isolated nucleic acid molecules that comprise a modified Murine Leukemia Virus Long Terminal Repeat which: a) comprises SEQ ID NO:4, SEQ ID NO:3, SEQ ID NO:2 or SEQ ID NO:1; b) is operably linked to a nucleotide sequence that encodes a non-Murine Leukemia Virus and c) is encapsulated within a liposome or a viral coat. The viral coat may be that of an infectious, replicating viral particle such as a retrovirus or a viral coat of an infectious, non-replicating viral package particle.

The present invention relates to methods of producing a non-Murine Leukemia Virus protein in an endothelial cell that comprises the step of introducing into said endothelial cell, nucleic acid molecule comprising a modified Murine Leukemia Virus Long Terminal Repeat which comprises SEQ ID NO:4, SEQ ID NO:3, SEQ ID NO:2 or SEQ ID NO:1 operably linked to a nucleotide sequence that encodes a non-Murine Leukemia Virus. In some embodiments, the cell is a human vessel endothelial cell. In some embodiments, the protein is a human protein such as for example: Factor VII protein, Factor IX protein, von Willdebrand factor, complement proteins, insulin, cytokines, tissue plasminogen activator, alpha-L-iduronidase, iduronate sulfatase, heparin, N-sulfatase and alpha 1 antitrypsin. In some embodiments, the nucleic acid molecule is encapsulated within a liposome or a viral coat. In some embodiments, the nucleic acid molecule is encapsulated within a viral coat of an infectious, replicating viral particle such as retrovirus particle. In some embodiments, the nucleic acid molecule is encapsulated within a viral coat of an infectious, non-replicating viral package particle. In some embodiments, the human vessel endothelial cells are in an individual. In some embodiments, the human vessel endothelial cells are in an individual and the nucleic acid molecule is delivered intravenously to the individual. In some embodiments, the human vessel endothelial cells are in an individual, the nucleic acid molecule is delivered intravenously to the individual and the nucleic acid molecule comprises a modified Murine Leukemia Virus Long Terminal Repeat which: a) comprises SEQ ID NO:4, SEQ ID NO:3, SEQ ID NO:2 or SEQ ID NO:1; b) is operably linked to a nucleotide sequence that encodes a non-Murine Leukemia Virus and c) is encapsulated within a liposome or a viral coat. The viral coat may be that of an infectious, replicating viral particle such as a retrovirus or a viral coat of an infectious, non-replicating viral package particle.

DETAILED DESCRIPTION OF THE INVENTION

As used herein, the term "tropism" is meant to refer to gene expression which takes place in a cell specific manner.

In particular, the term "endothelial cell tropism" is meant to refer to expression of coding sequences of nucleic acid molecules which occurs in endothelial cells only. Thus, the term "endothelial cell tropic compositions" refers to nucleic acid molecules which are specifically expressed in endothelial cells to the exclusion of other cells.

It has been discovered that modified forms of the long terminal repeat (LTR) of murine leukemia virus (MuLV) provides vessel endothelial cell tropic gene expression. According to the invention, MuLV LTR sequences which contain specific nucleotide sequences confer vessel endothelial cell tropism for expression of non-MuLV coding sequences operably linked to such modified LTR sequences. When operably linked to the modified LTRs of the invention, nucleotide sequences that encode non-MuLV proteins will be expressed at a high level in vessel endothelial cells but not in other cell types.

In previously studied systems, MuLV LTRs that have been observed to regulate expression in endothelial do not do so exclusively of expression in other cell types. That is, endothelial cell expression is not exclusive but rather is just one of many cell types in which the regulatory elements are functional. The present invention allows for gene expression specifically and exclusively in vessel endothelial cells. According to the present invention, modified MuLV LTRs of the invention, such as the MuLV LTR molecular clone TR1.3, may be used to express non-MuLV proteins in vessel endothelial cells but not in other cell types which have the MuLV/non-MuLV constructs. According to the present invention, the modified MuLV LTRs may be used in genetic constructs useful in gene therapy which are particularly directed at expressing genes in endothelial cells. Regardless of what other cell types take up the constructs of the invention, only the vessel endothelial cells which take up the construct will be capable of expressing the non-MuLV protein encoded by the sequence operably linked to the vessel endothelial cell tropic LTR of the invention.

According to some preferred embodiments, the modified MuLV LTR is a MuLV LTR in which nucleotides 131–200 of the LTR are SEQ ID NO:4. According to some preferred embodiments, the modified MuLV LTR is a Friend MuLV LTR in which nucleotides 131–200 of the LTR are SEQ ID NO:4.

According to some preferred embodiments, the modified MuLV LTR is a MuLV LTR in which nucleotides 101–200 of the LTR are SEQ ID NO:3. According to some preferred embodiments, the modified MuLV LTR is a Friend MuLV LTR in which nucleotides 101–200 of the LTR are SEQ ID NO:3.

According to some preferred embodiments, the modified MuLV LTR is a MuLV LTR in which the U3 region is SEQ ID NO:2. According to some preferred embodiments, the modified MuLV LTR is a Friend MuLV LTR in which the U3 region is SEQ ID NO:2.

According to some preferred embodiments, the modified MuLV LTR is a MuLV LTR in which nucleotides 1–415 of the LTR are SEQ ID NO:2. According to some preferred embodiments, the modified MuLV LTR is a Friend MuLV LTR in which nucleotides 1–415 of the LTR are SEQ ID NO:2.

According to some preferred embodiments, the modified MuLV LTR is a modified Friend MuLV LTR having SEQ ID NO:1. SEQ ID NO:1 is the LTR from the molecular clone TR1.3, which is a Friend MuLV.

LTRs of retroviruses function as both a promoter/enhancer element as well as a polyadenylation signal. Accordingly, LTRs may be used upstream and downstream of the coding sequence to provide the necessary regulatory sequences for transcription. According to the present invention, LTRs are operably linked upstream and/or downstream of the coding sequence. In genetic contructs which are delivered as linear constructs, the construct contains a modified LTR sequence of the invention upstream of and operably linked to a coding sequence that encodes a non-MuLV protein. In genetic contructs which are delivered as circular constructs, the construct contains a modified LTR sequence of the invention downstream of and operably linked to a coding sequence that encodes a non-MuLV protein. In both linear and circular constructs, the modified LTR of the invention as insered is operably linked to and upstream of the a coding sequence that encodes a non-MuLV protein. Those of ordinary skill in the art can freadily design vectors and constructs whereby the modified LTR of the invention is operably linked to and upstream of the a coding sequence that encodes a non-MuLV protein when the non-MuLV protein is being expressed tropically in vessel endothelial cells.

According to some preferred embodiments, the modified MuLV LTR is linked to the coding sequence that encodes a non-MuLV protein at a location 3' of the coding sequence. According to some preferred embodiments, two modified MuLV LTRs are linked to the coding sequence that encodes a non-MuLV protein; one at a location 3' of the coding sequence, and one at a location 5' of the coding sequence.

SEQ ID NO:1 contains a nucleotide sequence of a modified MuLV LTR, specifically the LTR from MuLV TR1.3. This nucleotide sequence is presented as a cDNA sequence of the genomic RNA of the virus. The modified LTR disclosed in SEQ ID NO:1 lacks three binding sites, FVb1, FVa and FVb2, as compared with the LTR of wild type Friend MuLV which replicates poorly or not at all in endothelial cells. The modified LTRs according to the present invention include MuLV LTRs which contain deletions, insertions and substitutions and which are capable of regulating endothelial cell specific expression of coding sequences operably linked thereto. Examples include SEQ ID NO:1. Modified LTRs according to the present invention include fragments of SEQ ID NO:1 which are capable of regulating endothelial cell specific expression of coding sequences operably linked thereto. SEQ ID NO:2 provides nucleotides 1–415 of SEQ ID NO:1. This sequence is the U3 region of the LTR and contains the portion of the LTR which is responsible for the vessel endothelial cell tropism which render the LTR particularly useful. SEQ ID NO:3 provides nucleotides 101–200 of SEQ ID NO:1. This sequence contains the portion of the LTR which is responsible for the vessel endothelial cell tropism which render the LTR particularly useful. SEQ ID NO:4 provides nucleotides 131–200 of SEQ ID NO:1. This sequence contains the portion of the LTR which is responsible for the vessel endothelial cell tropism which render the LTR particularly useful.

One having ordinary skill in the art can determine whether or not a modified MuLV LTR is capable of vessel endothelial cell tropic expression of coding sequences operably linked thereto using standard techniques and readily available starting materials without undue experimentation. For example, the nucleic acid molecule can be constructed that comprises modified LTRs operably linked to a reporter gene. A reporter gene is a gene which encodes a protein product that can be detected. Examples of common reporter genes include beta-galactosidase or chloramphenicol acetyl transferase. Simple assays are available to detect the presence of the protein product of these reporter genes. The nucleic acid molecule is transfected into endothelial cells and detection of the reporter gene product indicates that the LTRs are functioning in the cells. The nucleic acid molecule is transfected into non-endothelial cells. If the reporter gene product is not detected, the LTRs are not functioning in those cells. Primary endothelial cell cultures are best suited for in vitro expression of foreign genes. These cultures are easily obtained from human umbilical cord using standard techniques.

Modified LTRs, such as the modified LTR disclosed in SEQ ID NO:1, or a modified MuLV which comprises SEQ ID NO:2, SEQ ID NO:3, SEQ ID NO:4, or a functional fragment thereof, may be operably linked to nucleotide sequences which encode non-MuLV proteins to form a functional chimeric gene. When introduced into endothelial cells, the chimeric gene can be expressed to produce the protein in the endothelial cells. In particular, one or two copies of a modified MuLV LTRs such as that which is disclosed in SEQ ID NO:1 or a modified MuLV which comprises SEQ ID NO:2, SEQ ID NO:3, SEQ ID NO:4 or a functional fragment thereof may be operably linked to a nucleotide sequence that encodes a human protein in order to express the human protein in human vessel endothelial cells. In some embodiments, one copy is provided and it is linked upstream of the coding sequence. In some embodiments, one copy is provided and it is linked downstream of the coding sequence. In some embodiments, two copies are provided, one is linked upstream of the coding sequence and one copy is linked downstream.

In addition to a vessel endothelial tropic modified MuLV LTR operable linked to a coding sequence encoding a non-MuLV protein, gene constructs according to the invention may additionally comprise nucleotide sequences encoding signal sequences and other amino acid sequences linked to the non-MuLV protein sequence to direct secretion or intracellular location of the protein. Signal sequences which direct secretion of protein by endothelial cells are well known and those having ordinary skill in the art can readily design gene construct to express non-MuLV proteins in vessel endothelial cells by placing the coding sequence under the regulatory control of a modified MuLV LTR and further directing secretion of the non-MuLV protein so expressed in the vessel endothelial cells. Secretion by vessel endothelial cells can be specifically directed to result in luminal or abluminal secretion. Further, gene constructs can be designed so that the non-MuLV protein contains a transmembrane amino acid sequence. Such proteins will be anchored into the cell membrane of the vessel endothelial cell.

In some embodiments, gene constructs provide for delivering coding sequences that encode non-MuLV proteins into primary cells to express such proteins in primary vessel endothelial cells only. In some embodiments, the non-MuLV protein confers antibiotic resistance. Delivery of the gene construct to primary cell cultures results in expression of the non-MuLV protein in vessel endothelial cells only. Culturing the cells in selection medium, i.e. medium that contains the antibiotic will result in the death of all cells except those expressing the resistance gene. Thus, only the vessel endothelial cells will survive and the resulting culture will be pure primary vessel endothelial cells. The present invention is thus useful for expressing proteins in primary vessel endothelial cells and in some embodiments, for selectively culturing such cells. Transport and secretion of proteins in endothelial cells and the signals and peptide domains associated therewith are discussed in Rodriguez-Boulan, E. and C. Zurzolo 1993 *J. Cell Sci. Suppl.* 17:9–12 and Rodriguez-Boulan, E. and S. K. Powell 1992 *Annu. Rev. Cell Biol.* 8:395–427, each of which is incorporated herein by reference.

In some embodiments, construct may be useful in gene therapy applications in which gene expression and protein production in vessel endothelial cells is desired. The non-MuLV proteins which may be produced in endothelial cells according to the present invention include human and non-human proteins. Examples of human proteins which may be produced in endothelial cells according to the present invention include, but are not limited to Factor VII protein, Factor IX protein, von Willdebrand factor, complement proteins, insulin, cytokines, tissue plasminogen activator, alpha-L-iduronidase, iduronate sulfatase, heparin, N-sulfatase and alpha 1 antitrypsin. Factor VII protein is useful to treat individuals suffering from Hemophilia A. Factor IX protein is useful to treat individuals suffering from Hemophilia B. von Willdebrand factor is useful to treat individuals suffering from von Willdebrand's disease. Complement proteins are useful to treat individuals suffering from complement related immunodeficiencies. Insulin is useful to treat individuals suffering from diabetes. Cytokines are useful to treat individuals suffering from cancer, HIV infection and hereditary anemias among other conditions. Tissue plasminogen activator is useful in fibrinolytic therapy and in the prevention of stroke due to emboli. Alpha-L-iduronidase, iduronate sulfatase, heparin, N-sulfatase are useful to treat individuals suffering from mucopolysacharidoses and CNS and related disorders. Alpha 1 antitrypsin is useful to treat individuals suffering from alpha 1 antitrypsin deficiency and lung and related disorders.

According to some preferred embodiments, the coding sequence for human nerve growth factor is provided in gene construct. Delivery of the gene construct results in production of human NGF in vessel endothelial cells, facilitating renervation when delivered at or near wound sites.

According to some preferred embodiments, the coding sequence for human Factor IX is provided in gene construct. Delivery of the gene construct, particularly intravenously to individual suffering from hemophilia, results in production of Factor IX in vessel endothelial cells. Signal sequences may be provided to direct the Factor IX thus expressed to be secreted. Secretion of the Factor IX protein provides the individual with the necessary proteins for effective clotting.

According to other contemplated embodiments, nucleotide sequences encoding proteases, digestive enzymes and the like delivered are provided in gene construct. Delivery of the gene construct, particularly intravenously to an individual suspected to be at risk of suffering from or being susceptible to vessel occlusion results in production of the proteins in vessel endothelial cells. Transmembrane sequences may be provided to direct the location of the protein as being anchored in the blood vessel wall. The protein provides the individual with the necessary proteins to effectively prevent or reduce occlusion.

The ability to construct nucleic acid molecules, including the genomes of vectors, that exhibit tissue specific tropism will greater facilitate the applicability of human gene therapy. The ability to construct nucleic acid molecules, including the genomes of vectors, that can be transcriptional active in vessel endothelial cells exclusively are particularly useful for delivering proteins systemically through vascular vessel endothelial tissue or proteins directed at hematological or vascular disorders.

According to the present invention, vessel endothelial cells can be used to produce proteins while other cell types in which the gene constructs are also delivered do not express the protein. Vessel endothelial cells in the brain are particularly useful for expressing chimeric genes which comprise modified MuLV LTRs according to the invention.

According to one aspect of the present invention, non-MuLV proteins may be produced in vessel endothelial cells by introducing into the vessel endothelial cells a chimeric gene which includes a modified LTR operably linked to a nucleotide sequence which encodes the non-MuLV protein operably linked to a modified LTR. Introduction of the chimeric gene into the vessel endothelial cell will result in the expression of the nucleotide sequence that encodes the non-MuLV protein and, accordingly, the production of the non-MuLV protein.

According to some aspects of the present invention, the human vessel endothelial cells are targeted for production of non-MuLV proteins that are useful as therapeutics. In particular, the chimeric gene which includes modified LTRs operably linked to the nucleotide sequence that encodes the non-MuLV protein is delivered to the vessel endothelial cells of an individual by way of a vector or other vehicle.

For example, the chimeric gene may be part of a viral vector genome. Such viral vector genomes include those of retroviruses and DNA viruses which comprise the chimeric gene. An example of a viral vector system is Miller et al. 1993 Methods of Enzymol. 217:581–599, which is incorporated herein by reference. The nucleic acid sequence of such viral vectors are encapsulated within a viral particle made up of viral proteins. The viral particle is used to facilitate entry of the nucleic acid molecule that comprises the chimeric gene into the endothelial cell. Once inside the cell, the chimeric gene is expressed and the protein is produced.

Other methods of introducing nucleic acid molecules into cells are well-known to those having ordinary skill in the art. For example, nucleic acid molecules encapsulated within liposomes may be used to facilitate entry of the nucleic acid molecule into an endothelial cells. Liposomes are particularly useful because they have been shown to specifically target endothelial cells for the delivery of nucleic acid molecules encapsulated therein. Accordingly, the combination of liposomes with the chimeric gene comprises a modified MuLV LTR is particularly useful for delivering chimeric nucleic acid molecules to endothelial cells and expressing the coding sequences of chimeric genes. The production of liposome encapsulated gene constructs and there administration in vivo as well as the specific utility of liposomes for delivering nucleic acid molecules to endothelial cells has been pointed out in Zhu, N. et al. (1993) SCIENCE 261:209–211, which is incorporated herein by reference. Additionally, Debs, R. J. et al. (1990) J. Biol. Chem. 265(18):10189–10192, which has been incorporated herein by reference, teaches liposome production and administration of liposome encapsulated compositions.

The gene constructs may be prepared as plasmid DNA, linear DNA or RNA, as part of viral genomes, or as nucleic acid, molecules within viral packages. Viral packaging is well known and refers to a particular type of viral vector which is a infectious, non-replicating agent comprising a nucleic acid molecule such as a gene construct within a viral coat. Viral packages thus provide a means of delivery gene constructs into cells by providing viral-like particles which attach and introduce nucleic acid molecules into cells. However, instead of delivering a viral genome capable of directing viral replication, the nucleic acid molecule delivered by the particle is a gene construct which, in the present invention, encodes a non-MuLV protein whose expression is directed and regulated by the modified MuLV LTR. In packaging systems, cells express the proteins which make up the viral coat and additionally comprise genetic information to replicate the gene construct. The copies of the gene construct which are produced are packaged into the viral coat, yielding particles useful to deliver the gene construct into cells of an individual. However, once introduced into the cells, the particles cannot replicate. Examples of viral packaging systems include Markowitz et al. 1988 J. Virol. 62:1120–1124, which is incorporated herein by reference.

In some preferred embodiments, the gene construct is packaged in an amphotropic line. An amphotropic line will deliver gene constructs into all cells. The nature of viral coats is that they require a cellular receptor for which to attach. Amphotropic packaging lines produce viral particles which can attach to most or all cells. In some preferred embodiments, the gene construct is packaged in an amphotropic line in which the glycoprotein and env proteins of AM12 are expressed.

In some preferred embodiments, the gene constructs are administered intravenously. In some preferred embodiments, the gene constructs are packaged in an amphotropic line and delivered intravenously. In some preferred embodiments, $10^4$ to $10^6$ viral package particles are administered to an individual. In some preferred embodiments, about $10^5$ viral package particles are administered to an individual.

In one embodiment of the present invention a chimeric gene is constructed with comprises the modified MuLV LTR as disclosed in SEQ ID NO:1 operably linked to a nucleic acid sequence which encodes human Factor VII protein. The nucleic acid sequence which encodes human Factor VII protein is disclosed in O'Hara, P. J., et al. (1987) Proc. Natl. Acad. Sci. USA 84:5158–5162, which is incorporated herein by reference.

In one embodiment of the present invention a chimeric gene is constructed with comprises the modified MuLV LTR as disclosed in SEQ ID NO:1 operably linked to a nucleic acid sequence which encodes human Factor IX protein. The nucleic acid sequence which encodes human Factor IX protein is disclosed in Yao, S. et al. (1991) Proc. Natl. Acad. Sci. USA 88:8101–8105, which is incorporated herein by reference.

In some embodiments of the invention, the chimeric gene is inserted into retroviral vectors using a complementation system using vectors such as SV-psi⁻-env⁻-MLV and SV-psi⁻-A-MLV. These vectors are disclosed in Landau, N. R. and D. R. Littman (1992) J. Virol. 66(8):5110–5114, which is incorporated herein by reference.

We claim:

1. An isolated nucleic acid molecule comprising a modified Murine Leukemia Virus Long Terminal Repeat which comprises SEQ ID NO:4.

2. The nucleic acid molecule of claim 1 wherein said modified Murine Leukemia Virus Long Terminal Repeat sequence comprises SEQ ID NO:3.

3. The nucleic acid molecule of claim 1 wherein said modified Murine Leukemia Virus Long Terminal Repeat sequence comprises SEQ ID NO:2.

4. The nucleic acid molecule of claim 1 wherein said modified Murine Leukemia Virus Long Terminal Repeat sequence comprises SEQ ID NO:1.

5. The nucleic acid molecule of claim 1 wherein said modified Murine Leukemia Virus Long Terminal Repeat sequence comprises SEQ ID NO:4 and is operably linked to a nucleotide sequence that encodes a non-Murine Leukemia Virus protein.

6. The nucleic acid molecule of claim 1 wherein said modified Murine Leukemia Virus Long Terminal Repeat sequence comprises SEQ ID NO:3 and is operably linked to a nucleotide sequence that encodes a non-Murine Leukemia Virus protein.

7. The nucleic acid molecule of claim 1 wherein said modified Murine Leukemia Virus Long Terminal Repeat sequence comprises SEQ ID NO:2 and is operably linked to a nucleotide sequence that encodes a non-Murine Leukemia Virus protein.

8. The nucleic acid molecule of claim 1 wherein said modified Murine Leukemia Virus Long Terminal Repeat Sequence comprises SEQ ID NO:1 and is operably linked to a nucleotide sequence that encodes a non-Murine Leukemia Virus protein.

9. The nucleic acid molecule of claim 5 wherein said non-Murine Leukemia Virus protein is a human protein.

10. The nucleic acid molecule of claim 5 wherein said non-Murine Leukemia Virus protein is a human protein selected from the group consisting of: Factor VII protein, Factor IX protein, von Willdebrand factor, complement proteins, insulin, cytokines, tissue plasminogen activator, alpha-L-iduronidase, iduronate sulfatase, heparin, N-sulfatase and alpha 1 antitrypsin.

11. The nucleic acid molecule of claim 5 wherein said nucleic acid molecule is encapsulated within a liposome or a viral coat.

12. The nucleic acid molecule of claim 11 wherein said nucleic acid molecule is encapsulated within a liposome.

13. The nucleic acid molecule of claim 5 wherein said nucleic acid molecule is encapsulated within a viral coat.

14. The nucleic acid molecule of claim 13 wherein said nucleic acid molecule is incorporated within a viral genome.

15. The nucleic acid molecule of claim 13 wherein said nucleic acid molecule is incorporated with a retroviral genome.

16. The nucleic acid molecule of claim 13 wherein said nucleic acid molecule is encapsulated in an infectious, non-replicating virus package particle.

17. A method of producing a non-Murine Leukemia Virus protein in an endothelial cell that comprises the step of:

introducing into said endothelial cell, nucleic acid molecule comprising a modified Murine Leukemia Virus Long Terminal Repeat which comprises SEQ ID NO:4 operably linked to a nucleotide sequence that encodes a non-Murine Leukemia Virus protein.

18. The method of claim 17 wherein said cell is a human vessel endothelial cell.

19. The method of claim 17 wherein said modified Murine Leukemia Virus Long Terminal Repeat sequence comprises SEQ ID NO:3.

20. The method of claim 17 wherein said modified Murine Leukemia Virus Long Terminal Repeat sequence comprises SEQ ID NO:2.

21. The method of claim 17 wherein said modified Murine Leukemia Virus Long Terminal Repeat sequence comprises SEQ ID NO:1.

22. The method of claim 17 wherein said non-Murine Leukemia Virus protein is a human protein.

23. The method of claim 17 wherein said non-Murine Leukemia Virus protein is a human protein selected from the group consisting of Factor VII protein, Factor IX protein, von Willdebrand factor, complement proteins, insulin, cytokines, tissue plasminogen activator, alpha-L-iduronidase, iduronate sulfatase, heparin, N-sulfatase and alpha 1 antitrypsin.

24. The method of claim 17 wherein said nucleic acid molecule is encapsulated within a liposome or a viral coat.

25. The method of claim 11 wherein said nucleic acid molecule is encapsulated within a viral coat of a retrovirus particle.

26. The method of claim 11 wherein said nucleic acid molecule is encapsulated within a viral coat of an infectious, non-replicating viral package particle.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 574 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| AATGAAAGAC | CCCACCAAAT | TGCTTAGCCT | GATAGCCGCA | GTAACGCCAT | TTTGCAAGGC | 60 |
| ATGGAAAAAT | ACCAAACCAA | GAATAGAGAA | GTTCAGATCA | AGGGCGGGTA | CACGAAAACA | 120 |
| GCTAACGTTG | GGCCAAACAG | GATATCTGCG | GTGAGCAGTT | TCGGCCCCGG | CCCGGGCGAA | 180 |
| GAACAGATGG | TCACCGCAGT | TCGGCCCCGG | CCCGGGCGAA | GAACAGATGG | TCCCCAGATA | 240 |
| TGGCCCAACC | CTCAGCAGTT | TCTTAAGACC | CATCAGATGT | TTCCAGGCTC | CCCCAAGGAC | 300 |
| CTGAAATGAC | CCTGTGCCTT | ATTTGAATTA | ACCAATCAGC | CTGCTTCTCG | CTTCTGTTCG | 360 |
| CGCGCTTCTG | CTTCCCTAGC | CCTATAAAAG | AGCTCACAAC | CCCTCACTCG | GCGCGCCAGT | 420 |
| CCTCCGACAG | ACTGAGTCGC | CCGGGTACCC | GTGTATCCAA | TAAATCCTCT | TGCTGTTGCA | 480 |
| TCCGACTCGT | GGTCTCGCTG | TTCCTTGGGA | GGGTCTCCTC | AGAGTGATTG | ACTACCCGTC | 540 |
| TCGGGGTCT | TTCATTTGGG | GGCTCGTCCG | GGAT | | | 574 |

( 2 ) INFORMATION FOR SEQ ID NO:2:

( i ) SEQUENCE CHARACTERISTICS:
( A ) LENGTH: 415 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| AATGAAAGAC | CCCACCAAAT | TGCTTAGCCT | GATAGCCGCA | GTAACGCCAT | TTTGCAAGGC | 60 |
| ATGGAAAAAT | ACCAAACCAA | GAATAGAGAA | GTTCAGATCA | AGGGCGGGTA | CACGAAAACA | 120 |
| GCTAACGTTG | GGCCAAACAG | GATATCTGCG | GTGAGCAGTT | TCGGCCCCGG | CCCGGGCGAA | 180 |
| GAACAGATGG | TCACCGCAGT | TCGGCCCCGG | CCCGGGCGAA | GAACAGATGG | TCCCCAGATA | 240 |
| TGGCCCAACC | CTCAGCAGTT | TCTTAAGACC | CATCAGATGT | TTCCAGGCTC | CCCCAAGGAC | 300 |
| CTGAAATGAC | CCTGTGCCTT | ATTTGAATTA | ACCAATCAGC | CTGCTTCTCG | CTTCTGTTCG | 360 |
| CGCGCTTCTG | CTTCCCTAGC | CCTATAAAAG | AGCTCACAAC | CCCTCACTCG | GCGCG | 415 |

( 2 ) INFORMATION FOR SEQ ID NO:3:

( i ) SEQUENCE CHARACTERISTICS:
( A ) LENGTH: 100 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:3:

-continued

```
AGGGCGGGTA CACGAAAACA GCTAACGTTG GGCCAAACAG GATATCTGCG GTGAGCAGTT        60

TCGGCCCCGG CCCGGGCGAA GAACAGATGG TCACCGCAGT                             100
```

( 2 ) INFORMATION FOR SEQ ID NO:4:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
GGCCAAACAG GATATCTGCG GTGAGCAGTT TCGGCCCCGG CCCGGGCGAA GAACAGATGG        60

TCACCGCAGT                                                              70
```